(12) United States Patent
Lemcoff et al.

(10) Patent No.: US 9,718,849 B2
(45) Date of Patent: Aug. 1, 2017

(54) SULFUR CHELATED RUTHENIUM COMPOUNDS USEFUL AS OLEFIN METATHESIS CATALYSTS

(71) Applicant: BEN-GURION UNIVERSITY OF THE NEGEV RESEARCH AND DEVELOPMENT AUTHORITY, Be'er-Sheva (IL)

(72) Inventors: N. Gabriel Lemcoff, Yakum (IL); Amos Ben-Asuly, Doar Na Hanegev (IL)

(73) Assignee: BEN-GURION UNIVERSITY OF THE NEGEV RESEARCH AND DEVELOPMENT AUTHORITY, Be'er Sheva (IL)

( * ) Notice: Subject to any disclaimer, the term of this patent is extended or adjusted under 35 U.S.C. 154(b) by 227 days.

(21) Appl. No.: 13/945,189

(22) Filed: Jul. 18, 2013

(65) Prior Publication Data

US 2014/0155511 A1    Jun. 5, 2014

Related U.S. Application Data

(63) Continuation of application No. 12/609,051, filed on Oct. 30, 2009, now Pat. No. 8,513,151, which is a continuation-in-part of application No. 12/232,615, filed on Sep. 19, 2008, now abandoned.

(60) Provisional application No. 60/960,194, filed on Sep. 20, 2007.

(51) Int. Cl.

| C08F 2/50 | (2006.01) |
|---|---|
| C07F 15/00 | (2006.01) |
| C07D 211/96 | (2006.01) |
| C07C 67/333 | (2006.01) |
| C08G 61/08 | (2006.01) |
| C07C 61/20 | (2006.01) |
| C07D 207/48 | (2006.01) |
| C07D 223/04 | (2006.01) |
| C08F 4/80 | (2006.01) |

(52) U.S. Cl.
CPC .......... C07F 15/0046 (2013.01); C07C 61/20 (2013.01); C07C 67/333 (2013.01); C07D 207/48 (2013.01); C07D 211/96 (2013.01); C07D 223/04 (2013.01); C07F 15/0053 (2013.01); C08F 2/50 (2013.01); C08F 4/80 (2013.01); C08G 61/08 (2013.01); *C07C 2101/10* (2013.01)

(58) Field of Classification Search
CPC .... C08F 4/80; C08F 15/00; C08F 2/50; C07F 15/0046; C07D 207/48
See application file for complete search history.

(56) References Cited

U.S. PATENT DOCUMENTS

| 6,323,295 | B1 | 11/2001 | Muhlebach et al. |
| 6,921,735 | B2 * | 7/2005 | Hoveyda et al. ............. 502/152 |
| 2008/0275247 | A1 | 11/2008 | Kadyrov et al. |
| 2009/0156766 | A1 | 6/2009 | Lemcoff et al. |

OTHER PUBLICATIONS

Ben-Asuly et al., Amos, Organometallics 27, pp. 811-813, (2008).
Kost et al., Tamar, Journal of Organometallic Chemistry, No. 693, pp. 2200-2203, (2008).
Ben-Asuly et al., Amos, Organometallics 28, p. 4652-4622 (2009).

\* cited by examiner

*Primary Examiner* — Robert Harlan
(74) *Attorney, Agent, or Firm* — Nixon & Vanderhye P.C.

(57) ABSTRACT

Sulfur chelated ruthenium compounds represented by the following formula:

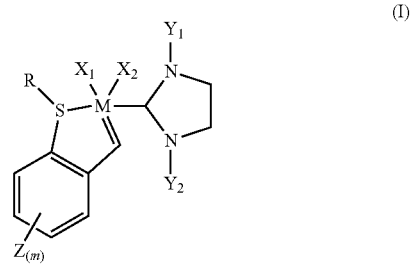

wherein M indicates the ruthenium metal bound to a benzylidene carbon; R represents $C_1$-$C_7$ alkyl group or optionally substituted aryl; $X_1$ and $X_2$ each independently represent halogen; $Y_1$ and $Y_2$ each independently denote unsubstituted or alkyl-substituted phenyl; and Z independently represents hydrogen, electron withdrawing or electron donating substituent, with m being an integer from 1 to 4, and processes and compositions related thereto.

14 Claims, 4 Drawing Sheets

SULFUR CHELATED RUTHENIUM COMPOUNDS USEFUL AS OLEFIN METATHESIS CATALYSTS

This application is a continuation of U.S. patent application Ser. No. 12/609,051, filed Oct. 30, 2009, which is a continuation-in-part of U.S. patent application Ser. No. 12/232,615, filed Sep. 19, 2008, which claims priority to U.S. Provisional Application No. 60/960,194, filed Sep. 20, 2007. The entire contents of each of which are incorporated herein by reference.

Olefin metathesis reactions are catalyzed by complexes of transition metals, such as ruthenium complexes. In such complexes, the metal atom is stabilized by means of suitable ligands and chelating groups, which provide the desired electronic and steric protecting environment to the metal. For example, in U.S. Pat. No. 6,921,735, Hoveyda et al. disclose the following ruthenium-based catalyst:

The compound depicted above (identified by Formula 5 in U.S. Pat. No. 6,921,735) is reported as an effective catalyst in ring-closing metathesis reactions of various dienes at room temperature, wherein the loading of said catalyst is 1 mol %.

The present invention relates to sulfur chelated ruthenium compounds represented by the following formula:

wherein M indicates the ruthenium metal bound to a benzylidene carbon; R represents $C_1$-$C_7$ alkyl group or optionally substituted aryl; $X_1$ and $X_2$ each independently represent halogen; $Y_1$ and $Y_2$ each independently denote unsubstituted or alkyl-substituted phenyl; and Z independently represents hydrogen, electron withdrawing or electron donating substituents, with m being an integer from 1 to 4. It should be noted that some of the bonds between the ruthenium and the surrounding ligands may be considered as coordinative bonds. In the formulas depicted hereinafter, arrows are sometimes used for pictorially illustrating such coordinative bonds.

Preferably, in the compounds represented by Formula I, $X_1$ and $X_2$ are both chlorine, $Y_1$ and $Y_2$ are both 2,4,6-trimethylphenyl (abbreviated Mes) and the aromatic ring is un-substituted in its four available positions, (namely, Z indicates hydrogen). Thus, an especially preferred class of compounds provided by the present invention has the following formula:

wherein R is selected from the group consisting of straight or branched $C_1$-$C_5$ alkyl (and specifically, methyl, ethyl, isopropyl and tertbutyl) and aryl (and specifically, phenyl, naphthyl and pyernyl).

The novel compounds of Formula (I) may be prepared by the following synthetic route:

A commercially available starting material of formula (1) which is a benzaldehyde derivative substituted at position 2 with a leaving group L, wherein L is preferably fluorine or chlorine, is reacted with a thiol RSH, wherein R has the above-mentioned meanings, in a suitable solvent, in the presence of a base. The starting material of formula (1), the thiol reactant and the base are generally used in approximately equimolar amounts, or more preferably, with a slight molar excess of the thiol and the base relative to the starting material of formula 1. Alternatively, the thiol is used in the form of its alkali salt, in which case the base may be omitted. The reaction is carried out under heating, wherein the reaction temperature is maintained at about 50-80° C. for about 1 to 4 days. Especially preferred solvents to be used are polar non-protonated solvents such as dimethyl formamide, dimethyl sulfoxide, dimethyl acetamide, tetrahydrofuran, etc. Bases operable in the reaction are weak non-nucleophilic bases, with the carbonates of alkali metals (e.g., potassium carbonate) being especially preferred. Upon completion of the reaction, the reaction mixture is cooled and the 2-thiobenzaldehyde derivative of formula (2) is isolated from the reaction mixture by means of extractive procedure. The solvent used for the extraction is then removed by evaporation, whereby an oily residue is obtained, which residue is typically purified by chromatography. Other conventional methods of isolation and purification may be applied in order to collect the 2-thiobenzaldehyde derivative of formula (2).

The 2-thiobenzaldehyde derivative of formula (2) is conveniently transformed to the corresponding alkene, namely, the 2-thio-styrene of Formula (3), through a Wittig reaction. To this end, a phosphonium salt of the formula $(C_6H_5)_3PCH_3Hal$, wherein Hal denotes halogen atom such as iodine or bromine, is treated with a strong base to form the corresponding ylid, triphenylphosphonium methylid. More specifically, the formation of the Wittig reagent is generally accomplished in a solvent such as diethyl ether, tetrahydrofuran or 1,4-dioxane, upon adding the phosphonium salt and a strong base such as potassium tert-butoxide or sodium hydride at about 0° C. and stirring the same for about 20 minutes at room temperature. Then, the 2-thiobenzaldehyde derivative of formula (2) is added at about 0° C. and mixed with the ylid at room temperature. For example, the 2-thiobenzaldehyde derivative may be added in one portion or in a stepwise manner to the reaction mixture containing the ylid. The progress of the reaction may be monitored by thin layer chromatography. The reactants are generally completely consumed after not more than 24 hours. The 2-thio-styrene of Formula (3) is then isolated from the reaction mixture by means of conventional techniques. Most conveniently, an aqueous solution of a saturated sodium bicarbonate is added to the reaction mixture followed by repeated extractions (using ether). The combined extracts are dried, the ether is removed by evaporation and the resulting 2-thio-styrene of Formula (3), in the form of colorless oil, is purified by chromatography.

The final step of the synthetic route involves a reaction of the 2-thio-styrene of Formula (3) with a ruthenium compound of Formula (4). In the compound of Formula (4), M stands for the ruthenium, and the substituents $X_1$, $X_2$, $Y_1$ and $Y_2$ have the same meanings mentioned before. The symbol $P(Cy)_3$ represents phosphine which contains three cyclic aliphatic moieties, namely, $C_5$ or $C_6$ rings, preferably tricyclohexyl phosphine. The preparation of compounds of Formula (4) is known in the art (for example, a compound of Formula 4 wherein $X_1$ and $X_2$ are both chlorine, $Y_1$ and $Y_2$ are both 2,4,6-trimethylphenyl is illustrated in Example 4 of U.S. Pat. No. 6,921,735 and Scholl, M.; Ding, S.; Lee, C. W.; Grubbs, R. H. Org. Lett. 1999, 1, 953-956). The preferred compound of Formula (4) to be used in the preparation of the novel compounds of Formula I is chemically named (1,3-Bis(2,4,6-trimethylphenyl)-2-imidazolidinylidene)dichloro(phenylmethylene)(tricyclohexylphosphine)ruthenium.

The reaction between the 2-thio-styrene of Formula (3) and a ruthenium compound of Formula (4) is conveniently carried out in halogenated hydrocarbon solvent, such as chlorinated alkanes, e.g., dichloromethane, in the presence of an agent capable of complexing and removing the phosphine ligand, thus allowing the complexation of the ruthenium metal with the new chelating, sulfur-containing ligand of Formula 3. A suitable agent in this regard is cuprous chloride CuCl. The concentration of each of the reactants in the solution is typically in the range between 20 mM to 300 mM, wherein the cuprous chloride is added in about 20% molar excess. The reaction is carried out under reflux for several hours, approximately 5-24 hours. The desired product is finally isolated by means of conventional techniques. For example, the reaction mixture is concentrated to dryness by evaporation, and the crude solid product is collected in the form of a powder. Alternatively, the compound of Formula I is caused to precipitate from the liquid phase of the reaction mixture by the addition of an anti-solvent, e.g., methanol, and is then separated by filtration. The resulting solid product may be purified by chromatography or recrystallization.

The general sequential reaction described above is illustrated for the preparation of the preferred compounds of Formula (1A) as follows, wherein the yield of each reaction step is also reported:

a - R = t-Bu
b - R = Ph
c - R = i-Pr
d - R = Et
e - R = Me

The preferred compounds according to the present invention are:
(1,3-Bis-(2,4,6-trimethylphenyl)-2-imidazolidinylidene)dichloro(o-tertthiobutoxyphenylmethylene)ruthenium (IAa)

(1,3-Bis-(2,4,6-trimethylphenyl)-2-imidazolidinylidene)di-
chloro(o-thiophenoxyphenylmethylene)ruthenium (IAb)

(1,3-Bis-(2,4,6-trimethylphenyl)-2-imidazolidinylidene)di-
chloro(o-isothiopropoxyphenylmethylene)ruthenium
(IAc)

(1,3-Bis-(2,4,6-trimethylphenyl)-2-imidazolidinylidene)di-
chloro(o-thioethoxyphenylmethylene)ruthenium (IAd)

(1,3-Bis-(2,4,6-trimethylphenyl)-2-imidazolidinylidene)di-
chloro(o-thiomethoxyphenylmethylene)ruthenium (IAe)

Additional preferred compounds which are prepared in a similar manner are:

(1,3-Bis-(2,4,6-trimethylphenyl)-2-imidazolidinylidene)di-
chloro(o-thionaphthoxyphenylmethylene)ruthenium
(IAf)

(1,3-Bis-(2,4,6-trimethylphenyl)-2-imidazolidinylidene)di-
chloro(o-thiopyernoxyphenylmethylene)ruthenium (IAg)

It is noted that in the compounds provided by the present invention, the existence of geometrical isomerism is possible whereas the chlorine ligands may be either in cis or trans positions relative to each other. While all possible isomers are within the scope of the invention, the sulfur chelated ruthenium compounds of Formula IA are more thermodynamically favored in the cis-dichloro geometrical conformation, as shown by their NMR spectra and confirmed by resolving their single crystal X-ray structure.

As mentioned above, in the compounds represented by Formula I, the aromatic ring may carry one to four electron withdrawing or electron donating substituents. Specifically, nitro and methoxy groups may be mentioned in this regard.

The sulfur chelated ruthenium compounds of this invention are useful in the catalysis of olefin metathesis reactions, namely, ring-closing metathesis (RCM), cross-metathesis (CM) and ring-opening metathesis polymerization (ROMP). In RCM reactions, a starting material which contains multiple carbon-carbon double bonds undergoes cyclization; namely, a diene is transformed to the corresponding cyclic alkene. In CM two different olefins are transformed into two additional olefins, in the case of terminal olefins usually ethylene is obtained and removed from the system. In ROMP reactions, a cyclic alkene starting material is polymerized, as schematically illustrated by the following schemes:

RCM

CM

ROMP wherein in the ROMP reaction scheme, T indicates the terminal group of the polymer.

It has been found that the sulfur chelated ruthenium compounds of the present invention display unique temperature-dependent reactivity profiles regarding the catalysis of olefin metathesis reactions. At room temperature, the compounds of the present invention are essentially catalytically inactive and cannot advance olefin metathesis reactions when combined with the olefin starting material (as quantifiably described herein below). However, the sulfur chelated ruthenium compounds can be thermally activated and deactivated alternately upon heating and cooling the reaction mixture, respectively. In other words, the present invention offers the advantage of thermally switching on and off the catalysis of olefin metathesis reaction by appropriately controlling the reaction temperature. The thermo-switchable behavior of the catalysts of the invention is specifically illustrated in detail in the examples herein below for two modes of olefin metathesis reactions: ring-closing of dienes and polymerization of cyclic alkenes.

Thus, in another aspect, the present invention provides a process, which comprises subjecting an olefin to a metathesis reaction in the presence of a catalytically effective amount of the compound of Formula I, and controlling the initiation and/or the progress of the reaction by thermally activating or deactivating said catalyst of Formula I, to form a reaction product.

The term "olefin" is used herein to indicate alkenes or cycloakenes which posses one or more carbon-carbon double bonds. Of course, the olefin starting material may include various chemical functional groups in addition to the carbon-carbon double bond(s). However, in the context of the process of the present invention the carbon-carbon double bonds of the starting material participate in the chemical reaction, and therefore the starting material is referred to herein as "olefin", regardless of its other functionalities.

Specifically, the olefin starting material may be a diene, in which case the metathesis reaction comprises the ring-closure of said diene to form a cyclic reaction product. Cyclic olefins which can be prepared according to the present invention may include 5-12 carbon atoms in the ring. More specifically, the process of the present invention may be useful in the preparation of precursors to natural products. For example, ring closing metathesis was the key step in the synthesis of coleophomone B and C (K. C. Nicolaou, G. Vassilikogiannakis, T. Angewandte Chemie 2002, 114, 3410-3415.)

Alternatively, the olefin starting material is cycloalkene and the metathesis reaction comprises the ring-opening polymerization of said cycloalkene to form a polymer. Polymerizable cyclic alkenes include norbornene and norbornene derivatives, cyclopentadiene and its derivatives, dicyclopentadiene and its derivatives, cyclooctene and its derivatives and cyclooctadiene and its derivatives.

The catalytically effective amount of the compound of Formula I used in the process of the present invention is generally not more than 5 mol % relative to the olefin starting material, though in many cases a catalytic loading of not more than 1 mol %, and even not more than 0.5 mol % (e.g., between 0.1 to 0.5 mol %) has been found to operate in a satisfactory manner, affording good conversion of the starting material.

The process of the present invention is typically run by dissolving the olefin starting material in a suitable inert solvent, adding the catalyst of Formula I to the resulting solution and mixing the same. The solvent, the olefin starting material and the catalyst may be fed to the reaction vessel in any desired order. The concentrations of the olefin starting material and the catalyst in the solution are preferably within the ranges of 50-500 mM and 0.05-5 mM, respectively.

Solvents to be used in the olefin metathesis reaction according to the process of the invention, include, but are not limited to, aromatic hydrocarbons (such as toluene, benzene and xylenes), halogenated hydrocarbons (such as dichloromethane, tetrachloroethane, dichloroethane, and chloroform) and ethers (such as tetrahydrofuran).

The reaction mixture containing the solvent, the olefin starting material and the catalyst is brought to the temperature required for thermally switching on the catalyst, which temperature is preferably within the range between 50 degrees centigrade and 100 degrees centigrade, and more preferably between 75 degrees centigrade and 85 degrees centigrade depending on the type of catalyst used. The reaction mixture may be held at the selected temperature for a sufficient time necessary to complete the reaction, with the progress of the reaction being monitored by means of GC-MS. However, the present invention offers the advantage of interrupting an uncompleted operation (whether conducted in a batch mode or a continuous mode) for long periods of time should this become necessary, in view of the fact that the reaction mixture is capable of standing for several hours, and even for several days without significant material change in composition. Thus, the catalysis of the metathesis reaction can be switched off by simply cooling the reaction mixture to about room temperature (either intentionally or unintentionally, in the event of a technical failure). During this intermission, no reaction product is essentially formed in the reaction mixture, while the compound of Formula I is surprisingly capable of preserving its potential catalytic reactivity, though kept in the reaction mixture under air. Following heating to above the threshold temperature, the compound of Formula I is reactivated, the catalysis is switched on and the metathesis reaction proceeds.

Upon completion of the reaction, the product is isolated and purified by conventional techniques such as evaporation, extraction, filtration and recrystallization and the catalyst may be recovered and recycled.

With the catalytic activity of the sulfur chelated ruthenium compounds being thermally switchable, it is now possible to provide a composition comprising an olefin starting material dissolved in an organic solvent (as listed above) together with a catalytically effective amount of the compound of Formula I, which composition is chemically stable at room temperature, such that the conversion of the olefin starting material through a metathesis reaction into a product is substantially controllable and even completely prevented at room temperature. By the term "substantially controllable" is meant that the conversion of the olefin starting material into a metathesis reaction product in the presence of the catalyst is less than 7.5%, when the two are stored together under ambient conditions for about 10-20 hours. Preferred catalysts of the invention (wherein R is C1-C3 alkyl or optionally substituted aryl, e.g., phenyl) exhibit increased stability profile, such that the conversion of an olefin starting material through a metathesis reaction into a product, when said olefin is kept in the presence of about 1 mol % catalyst loading, is less than 2% or even less than 1% at a temperature below 30° C. under storage for about 15 days, as determined by GC-MS. Preferably, when the composition of the present invention is stored under said ambient conditions, no traces of product are detected when the concentration of the catalyst is about 1 mol %. Thus, if desired, the reaction solvent, the olefin starting material and the catalyst may be safely mixed together in advance under ambient conditions or at a temperature below the threshold temperature necessary for activating the catalyst, to form a non-active mixture, and the metathesis reaction may be started at a later time upon heating said mixture to above said threshold temperature. It is noted that it is impossible to hold together under ambient conditions the reaction solvent, the olefin starting material and the catalyst represented by Formula 5 in U.S. Pat. No. 6,921,735:

since the metathesis reaction proceeds rapidly at room temperature.

It has been found that the catalytic activity of the sulfur chelated ruthenium compounds of formula (I) may also be induced by light irradiation, such that the metathesis reaction can be carried out at room temperature. The compounds of formula IA, wherein R is aryl (e.g., phenyl, naphthyl and pyrenyl), were found to be especially sensitive to light stimulus. When said compounds are combined with the olefin starting material at room temperature (15-35° C.), they respond to light irradiation by advancing the desired metathesis reaction (e.g., a conversion of a diene starting material through a ring-closing reaction to form the cyclic reaction product, or a conversion of a cycloalkene monomer through a ring-opening polymerization to the corresponding polymer).

Thus, the invention further provides a process for preparing a metathesis reaction product, which comprises subjecting an olefin to a metathesis reaction in the presence of a catalytically effective amount of the compound of Formula I as defined in claim 1, wherein R is an optionally substituted aryl, and irradiating said catalyst of Formula I with light.

The process is carried out by combining the olefin starting material and a catalytically effective amount of complex of Formula I in a suitable inert solvent, as set forth in detail above, and irradiating the resulting mixture, preferably at room temperature. It has been found that either ultraviolet (UV) or visible light may be applied for inducing the catalytic activity of the compound of formula I. The former type of irradiation is generally preferred, offering better yields of the desired product. Useful UV sources include xenon arc lamps, halogen lamps or lasers. Preferred wavelengths and irradiation intensities are in the ranges between 350 and 380 nm, and between 50 and 300 watts, respectively. In general, the irradiation period of the reaction mixture is in the range between 1 hour and 24 hours, preferably between 1 and 10 hours. Having terminated the irradiation, the reaction is allowed to continue at room temperature for an additional period of time, in order to reach completion. The progress of the metathesis reaction may be followed by means of gas chromatography-mass spectrometry (GC-MS) and NMR spectroscopy.

As mentioned hereinbefore, the complexes of formula I are generally provided in the cis-X1,X2 configuration (e.g., cis-dichloro geometry). It appears that the UV irradiation (and to a lesser extent, also the visible light irradiation) induces the isomerization of the compounds of formula IA, in particular when R is aryl, from the thermodynamically favored cis-X1,X2 form into the less stable trans-X1,X2 form. It is the latter isomer which exhibits the desired catalytic activity at room temperature. According to experimental evidence to date, the higher the amount of the trans isomer in the reaction mixture, the greater is the metathesis conversion. Accordingly, for each complex employed in the catalysis of the metathesis reaction, it is preferred to adjust the irradiation period such that the trans:cis ratio is maximized. The preferred complexes to be used according to the invention exhibit trans-cis ratio in the range between 1:5 and 1:2, more preferably between 1:3 and 1:2.5, following an irradiation period of not more than 10 hours.

It has been observed that a short heating period of a reaction mixture in which the compound of Formula I is present in the catalytically active trans configuration (especially wherein R is an optionally substituted aryl), results in a rapid transformation of said trans-isomer into the cis-isomer, and consequently, to the cessation of the reaction. It should be emphasized that the heating period of the reaction mixture is generally short, as the heating is intended to cause the trans→cis transformation, but not to induce a subsequent thermal activation of the cis-isomer according to the pathway outlined above. The desired temperature to which the reaction mixture should be brought in order to cause a complete trans→cis transformation and hence reaction cessation is generally above 50° C., e.g., between 50 and 150° C. Having kept the reaction mixture at said elevated temperature for a few minutes, the reaction mixture is cooled, e.g., approximately to room temperature. The resultant reaction mixture may be kept at room temperature for a long storage period, if desired. Following light irradiation, the reaction starts again, to produce additional amounts of the desired product. The fact that the compounds of Formula I, wherein R is aryl, can be readily activated and deactivated by light irradiation and subsequent heating, respectively, is advantageous from various perspectives (for example, when safety concerns dictate a rapid halting of the reaction). The activation-deactivation protocol offered by the invention allows greater flexibility in conducting metathesis reactions.

Thus, the invention also provides a process for carrying out a metathesis reaction wherein the reaction mixture is irradiated by light as set forth above, and is subsequently heated, whereby the reaction is terminated.

DEFINITIONS

The term aryl means a carbocyclic aromatic system containing one or more rings, wherein the rings may be attached together in a pendent manner or may be fused.

EXAMPLES

Methods

All reagents used were of reagent grade quality, purchased commercially from Sigma, Aldrich or Fluka and used without further purification. All solvents were dried and distilled prior to use. Purification by column chromatography was performed on Davisil Chromatographic silica media (40-6 μm). TLC analyses were performed using Merck pre-coated silica gel (0.2 mm) aluminum (backed)sheets.

Gas chromatography data was obtained using an Agilent 6850 GC equipped with a Agilent 5973 MSD working under standard conditions; and an Agilent HP5-MS column.

NMR spectra were recorded on Bruker DPX 200 or DPX 500 instruments. Chemical shifts, given in ppm, are relative to Me$_4$Si as the internal standard, or using the residual solvent peak.

Example 1

Preparation of 2-(isopropylsulfanyl)benzenecarbaldehyde 2-fluoro-benzaldehyde (2.00 g, 16.1 mmol), potassium carbonate (2.45 g, 17.1 mmol) and 2-propanethiol (1.35 g, 17.1 mmol) were dissolved in 10.0 mL DMF in a 50 mL round-bottomed flask under dry nitrogen, topped with a reflux condenser. The reaction mixture was heated to 50° C. for 48 h. After cooling the mixture was added to 50 mL of saturated potassium carbonate solution, and the mixture was extracted with 3×50 mL portions of ether. The extracts were dried with magnesium sulfate and evaporated. The yellow oil residue of the crude product was further purified by chromatography on silica gel using 95:5 petroleum ether (60-80) and dichloromethane as eluent to afford a yellow oil (2.58 g, 89%).

1-(isopropylsulfanyl)-2-vinylbenzene

Methyl triphenylphosphonium iodide (1.57 g, 3.88 mmol) was dissolved in 25 mL ether in a 50 mL round-bottomed flask at 0° C. under dry nitrogen. To the mixture was added in one portion potassium tert-butoxide (0.47 g, 4.16 mmol) and it was stirred for 10 min at room temperature. 2-(isopropylsulfanyl)benzenecarbaldehyde (0.50 g, 2.77 mmol) was added in one portion at 0° C. and the reaction mixture was stirred for additional 24 h at room temperature. The mixture was added to 50 mL of saturated sodium bicarbonate solution, and then was extracted with 3×50 mL portions of ether. The extracts were dried with magnesium sulfate and evaporated. The light yellow oil of the crude product was further purified by chromatography on silica gel using 95:5 petroleum ether 60-80 and ether as eluent to give a colorless oil (0.40 g, 81%).

The Compound of Formula 1a Wherein R is Isopropyl 1-(isopropylsulfanyl)-2-vinylbenzene (25.0 mg, 0.14 mmol), cuprous chloride (16.7 mg, 0.17 mmol) and (1,3-Bis(2,4,6-trimethylphenyl)-2-imidazolidinylidene)dichloro(phenylmethylene)(tricyclohexylphosphine)ruthenium (119 mg, 0.14 mmol) were dissolved in 6 mL dichloromethane in a 10 mL round-bottomed flask under dry nitrogen topped with a reflux condenser. The reaction mixture was refluxed for 4.5 h. The resulting mixture was evaporated to dryness. The crude product was purified by chromatography on silica gel using 7:3 n-hexane and acetone as eluent to give a teal solid (48.0 mg, 55%). Two additional byproducts were separated by chromatography, but only one was fully characterized by NMR analysis: the trans-catalyst isomer green solid (8.1 mg, 9%) and additional green solid (14.2 mg). Both spontaneously converted with time to product 1A according to NMR analysis. Crystals suitable for X-ray analysis were obtained by laying hexanes over a solution of 1A in dichloromethane for few days at −18° C.

$^1$H NMR (500 MHz, CD$_2$Cl$_2$): δ 0.76 (d, J=6.5 Hz, 3H), 1.41 (d, J=7.4 Hz, 3H), 1.56 (s, 3H), 2.16 (s, 3H), 2.37 (s, 3H), 2.44 (s, 3H), 2.57 (s, 3H), 2.64 (s, 3H), 3.58 (m, 1H), 3.80 (m, 1H), 3.88 (m, 1H), 4.00 (m, 1H), 4.11 (m, 1H), 5.96 (bs, 1H), 6.79 (d, J=7.5 Hz, 1H), 6.88 (bs, 1H), 7.04 (bs, 1H), 7.12 (bs, 1H), 7.17 (t, J=6.4 Hz, 1H), 7.46 (m, 2H), 17.14 (s, 1H) ppm. $^{13}$C NMR (125 MHz, CDCl$_3$): δ 17.7, 18.7, 19.7, 20.3, 20.9, 21.0, 21.3, 24.2, 39.0, 51.4, 51.6, 123.7, 128.6, 129.4, 129.6, 129.7, 129.8, 130.7, 131.7, 135.0, 135.4, 135.6, 137.3, 137.7, 138.5, 140.3, 140.4, 156.6, 213.6, 285.6 ppm. APCI-MS m/z (M-Cl)$^+$: 607.1 (Calc. 607.15).

Example 2

Preparation of 2-(methylsulfanyl)benzenecarbaldehyde 2-fluoro-benzaldehyde (2.00 g, 16.1 mmol), potassium carbonate (2.45 g, 17.7 mmol) and methyl sodium sulfide (17.1 mmol) were dissolved in 10.0 mL DMF in a 50 mL round-bottomed flask under dry nitrogen, topped with a reflux condenser. The reaction mixture was heated to 55° C. for 24 hr. After cooling, the mixture was added to 50 mL of saturated potassium carbonate solution and extracted with 3×50 mL portions of ether. The extracts were dried with magnesium sulfate and evaporated. The crude product was further purified by chromatography on silica gel using 1:1 dichloromethane/n-hexane as eluent to give a yellow oil (2.08 g, 85%). $^1$H NMR (200 MHz, CDCl$_3$): δ 2.49 (s, 3H), 7.24-7.58 (m, 3H), 7.80 (dd, J1=7.6, J2=1.4, 1H), 10.25 (s, 1H) ppm.

1-(methylsulfanyl)-2-vinylbenzene

Methyl triphenylphosphonium iodide (1.57 g, 3.88 mmol) was dissolved in 25 mL ether in a 50 mL round-bottomed flask under dry nitrogen. To the mixture was added in one portion at 0° C. potassium tert-butoxide (0.47 g, 4.19 mmol) and it was stirred for 10 min at room temperature. 2-(methylsulfanyl)benzenecarbaldehyde (2.77 mmol) was added in one portion at 0° C. and the reaction mixture was stirred until complete disappearance of the reactants (2 hr) at room temperature (followed by TLC). The mixture was added to 50 mL of saturated sodium bicarbonate solution, followed by extraction with 3×50 mL portions of ether. The extracts were dried with magnesium sulfate and evaporated. The crude product was further purified by chromatography on silica gel using petroleum ether 60-80 as eluent. Yield: 0.33 g, 79%, colorless oil. 1H NMR (200 MHz, CDCl$_3$): δ 2.43 (s, 3H), 5.32 (dd, J1=10.9, J2=1.2, 1H), 5.67 (dd, J1=17.4, J2=1.2, 1H), 7.05-7.26 (m, 4H), 7.46 (d, 1H) ppm.

The Compound of Formula 1A Wherein R is Methyl 1-(methylsulfanyl)-2-vinylbenzene (0.14 mmol), cuprous chloride (16.2 mg, 0.16 mmol) and (1,3-Bis(2,4,6-trimethylphenyl)-2-imidazolidinylidene)dichloro(phenylmethylene)(tricyclohexylphosphine)ruthenium (119 mg, 0.14 mmol) were dissolved in 6 mL dichloromethane in a 10 mL round-bottomed flask under dry nitrogen topped with a reflux condenser. The reaction mixture was refluxed for 24 h. The resulting mixture was evaporated to dryness and the crude product was purified by chromatography on silica gel using 7:3 n-hexane and acetone as eluent. Yield 44 mg (51%) grayish blue solid, $^1$H NMR (500 MHz, CD$_2$Cl$_2$): δ 1.58 (s, 3H), 2.16 (s, 3H), 2.37 (s, 3H), 2.41 (s, 3H), 2.47 (s, 3H), 2.50 (s, 3H), 2.64 (s, 3H), 3.82-3.88 (m, 1H), 3.91-3.97 (m, 1H), 3.99-4.05 (m, 1H), 4.11-4.17 (m, 1H), 6.03 (s, 1H), 6.82 (dd, J1=7.9, J2=1.2, 1H), 6.93 (s, 1H), 7.05 (s, 1H), 7.12 (s, 1H), 7.16 (dt, J1=7.3, J2=1.2, 1H), 7.47 (d, J=7.3, 1H), 7.51 (dt, J1=7.9, J2=7.3, J3=1.2, 1H), 17.00 (s, 1H) ppm. $^{13}$C NMR (125 MHz, CD$_2$Cl$_2$): δ 17.57, 18.21, 18.90, 19.15, 20.46, 21.20, 21.51, 51.70, 51.81, 123.85, 128.83, 129.47, 129.62, 129.80, 129.84, 129.89, 131.01, 131.85, 135.85, 137.06, 138.06, 138.87, 140.38, 140.41, 140.64, 155.32, 214.62, 285.55 ppm. FAB-MS: M+ calc. 614.1. found 614.1, [M-Cl]+ calc. 579.1. found 579.1.

Example 3

Preparation of 2-(ethylsulfanyl)benzenecarbaldehyde 2-fluoro-benzaldehyde (2.00 g, 16.1 mmol), potassium carbonate (2.45 g, 17.7 mmol) and thioethanol (17.1 mmol) were dissolved in 10.0 mL DMF in a 50 mL round-bottomed flask under dry nitrogen, topped with a reflux condenser. The reaction mixture was heated to 55° C. for 3 days. After cooling, the mixture was added to 50 mL of saturated potassium carbonate solution and extracted with 3×50 mL portions of ether. The extracts were dried with magnesium sulfate and evaporated. The crude product was further purified by chromatography on silica gel using 2:1 dichloromethane/n-hexane as eluent to give a yellow oil (1.94 g, 72%). $^1$H NMR (200 MHz, CDCl$_3$): δ 1.37 (t, J=7.5, 3H), 2.99 (q, J=7.5, 2H), 7.26-7.56 (m, 3H), 7.84 (dd, J1=8.0, J2=1.7, 1H), 10.37 (s, 1H) ppm.

1-(ethylsulfanyl)-2-vinylbenzene

Methyl triphenylphosphonium iodide (1.57 g, 3.88 mmol) was dissolved in 25 mL ether in a 50 mL round-bottomed flask under dry nitrogen. To the mixture was added in one portion at 0° C. potassium tert-butoxide (0.47 g, 4.19 mmol) and it was stirred for 10 min at room temperature. 2-(ethylsulfanyl)benzenecarbaldehyde (2.77 mmol) was added in one portion at 0° C. and the reaction mixture was stirred until complete disappearance of the reactants (22 hr) at room temperature (followed by TLC). The mixture was added to 50 mL of saturated sodium bicarbonate solution, followed by extraction with 3×50 mL portions of ether. The extracts were dried with magnesium sulfate and evaporated. The crude product was further purified by chromatography on silica gel using petroleum ether 60-80 as eluent. Yield: 0.37 g, 81%, colorless oil. $^1$H NMR (200 MHz, CDCl$_3$): δ 1.29 (t, J=7.3, 3H), 2.89 (q, J=7.3, 2H), 5.34 (dd, J1=10.9, J2=1.2, 1H), 5.69 (dd, J1=17.4, J2=1.2, 1H), 7.19-7.54 (m, 5H) ppm.

The Compound of Formula 1A Wherein R is Ethyl 1-(ethylsulfanyl)-2-vinylbenzene (0.14 mmol), cuprous chloride (16.2 mg, 0.16 mmol) and (1,3-Bis(2,4,6-trimethylphenyl)-2-imidazolidinylidene)dichloro(phenylmethylene)(tricyclohexylphosphine)ruthenium (119 mg, 0.14 mmol) were dissolved in 6 mL dichloromethane in a 10 mL round-bottomed flask under dry nitrogen topped with a reflux condenser. The reaction mixture was refluxed for 24 h. The resulting mixture was evaporated to dryness and the crude product was purified by chromatography on silica gel using 7:3 n-hexane and acetone as eluent. Yield: 80 mg, 91%, teal solid, $^1$H NMR (500 MHz, C$_2$D$_2$Cl$_4$): δ 1.18 (t, J=7.3, 3H), 1.47 (s, 3H), 2.20 (s, 3H), 2.36 (s, 3H), 2.51 (s, 3H), 2.53 (s, 3H), 2.73 (s, 3H), 2.73 (m, 1H), 3.20-3.27 (J1, J2, J3=7.3; J4=14.0, 1H), 3.78-3.85 (m, 1H), 3.91-4.02 (m, 2H), 4.11-4.18 (m, 1H), 6.05 (s, 1H), 6.78 (d, J=7.3, 1H), 6.95 (s, 1H), 7.01 (s, 1H), 7.12 (s, 1H), 7.18 (t, J=7.3, 1H), 7.50 (m, 2H), 17.15 (s, 1H) ppm. $^{13}$C NMR (125 MHz, C$_2$D$_2$Cl$_4$): δ 13.48, 17.08, 18.74, 19.44, 20.17, 20.89, 21.22, 30.80, 50.88, 51.14, 123.30, 128.82, 129.00, 129.05, 129.29, 129.33, 129.64, 130.69, 131.40, 135.06, 135.31, 136.31, 137.58, 138.19, 138.82, 139.40, 139.85, 154.71, 213.81 ppm. FAB-MS: M+ calculated 628.1. found 628.0, [M-Cl]+ calculated 593.1. found 593.1.

Example 4

Preparation of

2-(tert-butylsulfanyl)benzenecarbaldehyde 2-fluoro-benzaldehyde (2.00 g, 16.1 mmol), potassium carbonate (2.45 g, 17.7 mmol) and 2-methyl-2-propanethiol (17.1 mmol) were dissolved in 10.0 mL DMF in a 50 mL round-bottomed flask under dry nitrogen, topped with a reflux condenser. The reaction mixture was heated to 50° C. for 4 days. After cooling, the mixture was added to 50 mL of saturated potassium carbonate solution and extracted with 3×50 mL portions of ether. The extracts were dried with magnesium sulfate and evaporated. The crude product was further purified by chromatography on silica gel using 2:1 dichloromethane/n-hexane as eluent to give a yellow oil (1.26 g, 40%). $^1$H NMR (200 MHz, CDCl$_3$): δ 1.26 (s, 9H), 7.43-7.63 (m, 3H), 7.96 (dd, J1=6.9, J2=2.5, 1H), 10.76 (s, 1H) ppm.

1-(tert-butylsulfanyl)-2-vinylbenzene

Methyl triphenylphosphonium iodide (1.57 g, 3.88 mmol) was dissolved in 25 mL ether in a 50 mL round-bottomed flask under dry nitrogen. To the mixture was added in one portion at 0° C. potassium tert-butoxide (0.47 g, 4.19 mmol) and it was stirred for 10 min at room temperature. 2-(tert-butylsulfanyl)benzenecarbaldehyde (2.77 mmol) was added in one portion at 0° C. and the reaction mixture was stirred until complete disappearance of the reactants (24 hr) at room temperature (followed by TLC). The mixture was added to 50 mL of saturated sodium bicarbonate solution, followed by extraction with 3×50 mL portions of ether. The extracts were dried with magnesium sulfate and evaporated. The crude product was further purified by chromatography on silica gel using petroleum ether 60-80 as eluent. Yield: 0.37 g, 70%, colorless oil. $^1$H NMR (200 MHz, CDCl$_3$): δ 1.26 (s, 9H), 5.28 (dd, J1=11.0, J2=1.2, 1H), 5.68 (dd, J1=17.8, J2=1.2, 1H), 7.17-7.67 (m, 5H) ppm.

The Compound of Formula 1A Wherein R is Tert-Butyl 1-(tert-butylsulfanyl)-2-vinylbenzene (0.14 mmol), cuprous chloride (16.2 mg, 0.16 mmol) and (1,3-Bis(2,4,6-trimethylphenyl)-2-imidazolidinylidene)dichloro(phenylmethylene)(tricyclohexylphosphine)ruthenium (119 mg, 0.14 mmol) were dissolved in 6 mL dichloromethane in a 10 mL round-bottomed flask under dry nitrogen topped with a reflux condenser. The reaction mixture was refluxed for 24 h. The resulting mixture was evaporated to dryness and the crude product was purified by chromatography on silica gel using 7:3 n-hexane and acetone as eluent. Yield: 65 mg, 70%, grey-asparagus solid, $^1$H NMR (500 MHz, C$_2$D$_2$Cl$_4$): δ 1.30 (s, 9H), 1.48 (s, 3H), 2.18 (s, 3H), 2.34 (s, 3H), 2.51 (s, 3H), 2.59 (s, 3H), 2.77 (s, 3H), 3.73-3.80 (m, 1H), 3.85-3.91 (m, 1H), 3.93-3.99 (m, 1H), 4.09-4.15 (m, 1H), 5.96 (s, 1H), 6.79 (d, J=7.3, 1H), 6.90 (s, 1H), 7.03 (s, 1H), 7.13 (s, 1H), 7.17 (t, J1=7.9, J2=7.3, 1H), 7.50 (t, J=7.3, 1H), 7.61 (d, J=7.9, 1H), 17.43 (s, 1H) ppm. $^{13}$C NMR (125 MHz, C$_2$D$_2$Cl$_4$): δ 17.42, 18.93, 19.59, 20.30, 20.85, 21.10, 30.35, 50.99, 51.17, 53.72, 123.60, 128.56, 128.93, 129.00, 129.22, 129.49, 129.99, 130.70, 132.08, 134.91, 135.38, 136.52, 137.09, 137.58, 137.94, 139.39, 139.71, 155.55, 213.18, 288.80 ppm. FAB-MS: [M-Cl]+ calc. 621.2. found 621.1.

Example 5

Preparation of

2-(phenylsulfanyl)benzenecarbaldehyde 2-fluoro-benzaldehyde (2.00 g, 16.1 mmol), potassium carbonate (2.45 g, 17.7 mmol) and thiophenol (17.1 mmol) were dissolved in 10.0 mL DMF in a 50 mL round-bottomed flask under dry nitrogen, topped with a reflux condenser. The reaction mixture was heated to 80° C. for 24 hrs. After cooling, the mixture was added to 50 mL of saturated potassium carbonate solution and extracted with 3×50 mL portions of ether. The extracts were dried with magnesium sulfate and evaporated. The crude product was further purified by chromatography on silica gel using 9:1 petroleum ether 60-80 and dichloromethane as eluent to give a yellow oil (2.46 g, 71%). $^1$H NMR (200 MHz, CDCl$_3$): δ 7.07 (dd, J1=7.8, J2=1.2, 1H), 7.27-7.45 (m, 7H), 7.87 (dd, J1=7.3, J2=2.0, 1H), 10.37 (s, 1H) ppm.

1-(phenylsulfanyl)-2-vinylbenzene

Methyl triphenylphosphonium iodide (1.57 g, 3.88 mmol) was dissolved in 25 mL ether in a 50 mL round-bottomed flask under dry nitrogen. To the mixture was added in one portion at 0° C. potassium tert-butoxide (0.47 g, 4.19 mmol) and it was stirred for 10 min at room temperature. 2-(phenylsulfanyl)benzenecarbaldehyde (2.77 mmol) was added in one portion at 0° C. and the reaction mixture was stirred until complete disappearance of the reactants (17 hr) at room temperature (followed by TLC). The mixture was added to 50 mL of saturated sodium bicarbonate solution, followed by extraction with 3×50 mL portions of ether. The extracts were dried with magnesium sulfate and evaporated. The crude product was further purified by chromatography on silica gel using petroleum ether 60-80 as eluent. Yield: 0.53 g, 91%, colorless oil. $^1$H NMR (200 MHz, CDCl$_3$): δ 5.33 (dd, J1=10.9, J2=1.2, 1H), 5.74 (dd, J1=17.4, J2=1.2, 1H), 7.16-7.65 (m, 10H) ppm.

The Compound of Formula 1A Wherein R is Phenyl 1-(phenylsulfanyl)-2-vinylbenzene (0.14 mmol), cuprous chloride (16.2 mg, 0.16 mmol) and (1,3-Bis(2,4,6-trimethylphenyl)-2-imidazolidinylidene)dichloro(phenylmethylene)(tricyclohexylphosphine)ruthenium (119 mg, 0.14 mmol) were dissolved in 6 mL dichloromethane in a 10 mL round-bottomed flask under dry nitrogen topped with a reflux condenser. The reaction mixture was refluxed for 24 h. The resulting mixture was evaporated to dryness and the crude product was purified by chromatography on silica gel using 7:3 n-hexane and acetone as eluent. Yield: 75 mg, 79%, persian green solid. $^1$H NMR (500 MHz, $C_2D_2Cl_4$): δ 1.68 (s, 3H), 2.19 (s, 3H), 2.30 (s, 3H), 2.49 (s, 3H), 2.64 (s, 3H), 2.65 (s, 3H), 3.85-3.96 (m, 2H), 4.04-4.10 (m, 1H), 4.12-4.18 (m, 1H), 6.06 (s, 1H), 6.85-7.43 (m, 12H), 17.21 (s, 1H) ppm. $^{13}$C NMR (125 MHz, $C_2D_2Cl_4$): δ 17.32, 18.63, 19.32, 20.02, 20.89, 21.19, 51.15, 51.42, 123.12, 128.16, 128.22, 129.09, 129.12, 129.39, 129.45, 129.48, 129.57, 130.70, 131.76, 133.11, 135.19, 135.23, 135.89, 137.24, 138.27, 138.52, 139.11, 139.61, 154.50, 213.36, 284.95 ppm. FAB-MS: M+ calc. 676.1. found 676.0, [M-Cl]+ calc. 641.1. found 641.0.

Example 6

Preparation of 2-(isopropylthio)-5-nitrobenzaldehyde 2-chloro-5-nitrobenzaldehyde (2.99 g, 16.1 mmol), potassium carbonate (2.45 g, 17.7 mmol) and propane-2-thiol (1.35 g, 17.7 mmol) were dissolved in 10.0 mL DMF in a 50 mL round-bottomed flask under dry nitrogen, topped with a reflux condenser. The reaction mixture was heated to 55° C. for 24 h. After cooling the mixture was added to 150 mL of saturated potassium carbonate solution. The yellow-brown solid was filtered, washed with water and further purified by chromatography on silica gel using 10:1 petroleum ether 60-80 and ether as eluent. Yield: 1.81 g, 50%, yellow solid. $^1$H NMR (200 MHz, $CDCl_3$): δ 1.46 (d, J=6.9 Hz, 6H), 3.67 (septet, J=6.9 Hz, 1H), 7.55 (d, J=8.7 Hz, 1H), 8.32 (dd, J=2.5, 8.7 Hz, 1H), 8.66 (d, J=2.5 Hz, 1H), 10.3 (s, 1H) ppm. $^{13}$C NMR (50 MHz, $CDCl_3$): δ 22.5, 36.6, 127.2, 127.4, 127.9, 133.4, 144.7, 150.8, 189.1.

isopropyl(4-nitro-2-vinylphenyl)sulfane

Methyl triphenylphosphonium iodide (1.57 g, 3.88 mmol) was dissolved in 25 mL ether in a 50 mL round-bottomed flask at 0° C. under dry nitrogen. To the mixture was added in one portion potassium tert-butoxide (0.47 g, 4.16 mmol) and it was stirred for 10 min at room temperature. 2-(isopropylthio)-5-nitrobenzaldehyde (0.62 g, 2.77 mmol) was added in one portion at 0° C. and the reaction mixture was stirred for additional 4 h at room temperature. The mixture was added to 100 mL of saturated sodium bicarbonate solution, and then was extracted with 3×50 mL portions of ether. The extracts were dried with magnesium sulfate and evaporated. The crude product was further purified by chromatography on silica gel using 4:1 petroleum ether 60-80 and ether as eluent. Yield: 0.50 g, 81%, yellow oil. $^1$H NMR (200 MHz, $CDCl_3$): δ 1.37 (d, J=6.6 Hz, 6H), 3.56 (septet, J=6.6 Hz, 1H), 5.50 (dd, J=0.9, 10.9 Hz, 1H), 5.80 (dd, J=0.9, 17.2 Hz, 1H), 7.09 (dd, J=10.9, 17.2 Hz, 1H), 7.40 (d, J=8.7 Hz, 1H), 8.04 (dd, J=2.5, 8.7 Hz, 1H), 8.30 (d, J=2.5 Hz, 1H) ppm. $^{13}$C NMR (50 MHz, $CDCl_3$): δ 22.8, 37.1, 118.4, 120.9, 122.3, 128.2, 132.8, 138.4, 144.5, 145.5.

The Compound of Formula 1A Wherein R is Isopropyl, and Z is Nitro Group isopropyl(4-nitro-2-vinylphenyl)sulfane (31.3 mg, 0.14 mmol) cuprous chloride (16.7 mg, 0.17 mmol) and (1,3-Bis (2,4,6-trimethylphenyl)-2-imidazolidinylidene)dichloro (phenylmethylene)(tricyclohexylphosphine)ruthenium (119 mg, 0.14 mmol) were dissolved in 6 mL dichloromethane in a 38 mL close pressure tube under dry nitrogen. The reaction mixture was refluxed overnight. The resulting mixture was evaporated to 2-3 mL DCM. The crude product was purified by chromatography on silica gel using 7:3 n-hexane and acetone as eluent. Yield: 50 mg, 52%, dark green solid. $^1$H NMR (500 MHz, $CD_2Cl_2$): δ 0.83 (d, J=6.5 Hz, 3H), 1.50 (d, J=7.3 Hz, 3H), 1.60 (s, 3H), 2.09 (s, 3H), 2.13 (s, 3H), 2.39 (s, 3H), 2.46 (s, 3H), 2.58 (s, 3H), 2.63 (s, 3H), 3.78 (m, 1H), 3.84 (m, 1H), 3.91 (m, 1H), 4.04 (m, 1H), 4.14 (m, 1H), 6.02 (s, 1H), 6.98 (s, 1H), 7.06 (s, 1H), 7.14 (s, 1H), 7.63 (m, 2H), 8.34 (dd, J=2.2, 8.7 Hz, 1H), 17.18 (s, 1H) ppm. $^{13}$C NMR (125 MHz, $CD_2Cl_2$): δ 18.0, 18.9, 19.9, 20.5, 20.9, 21.3, 21.5, 24.4, 40.5, 51.7, 51.9, 117.3, 122.2, 128.7, 129.1, 130.1, 130.2, 130.7, 131.1, 131.3, 135.8, 137.3, 138.4, 139.8, 140.6, 141.0, 142.7, 149.7, 156.6, 212.4, 280.5 ppm. FAB-MS $C_{31}H_{37}C_{12}N_3O_2RuS$ [M]$^+$ 687.1. found 687.0.

Example 7

Preparation of

2-(3-naphtylsulfanyl)benzenecarbaldehyde

This reactant was synthesized according to the literature procedure in Zhang H. Q., Xia Z., Kolasa T., Dinges J. *Tetrahedron Letters* 2003, 44, 8661-8663.

1-(3-naphtylsulfanyl)-2-vinylbenzene

Methyl triphenylphosphonium iodide (1.56 g, 3.87 mmol) was dissolved in 25 mL ether in a 50 mL round-bottom flask at 0° C. under dry nitrogen. To the mixture was added in one portion potassium tert-butoxide (0.46 g, 4.15 mmol) and was stirred for 10 min at room temperature. 2-(3-naphtylsulfanyl)benzenecarbaldehyde (0.73 g, 2.77 mmol) was added in one portion at 0° C. and the reaction mixture was stirred for additional 2.5 h at room temperature. The mixture was added to 50 mL of saturated sodium bicarbonate solution, and extracted with 3×50 mL portions of ether. The extracts were dried with magnesium sulfate and evaporated. The light yellow oil of the crude product was further purified by chromatography on silica gel using 9:1 petroleum ether 60-80: ether as eluent to afford a colorless oil (0.58 g, 81%). $^1$H-NMR (500 MHz, CDCl3): δ 5.35 (dd, J=1.3, 11.0 Hz, 1H), 5.77 (dd, J=1.3, 17.5 Hz, 1H), 7.24-7.51 (m, 7H), 7.67-7.81 (m, 5H) ppm. $^{13}$C-NMR (125 MHz, CDCl3): δ 116.28, 125.85, 126.20, 126.50, 127.22, 127.48, 127.68, 127.97, 128.24, 128.49, 128.70, 131.91, 132.81, 133.72, 133.78, 133.81, 134.52, 139.71 ppm. EI-MS: m/z M+ Calc. 262.3. found 262.2.

The Compound of Formula 1A Wherein R is Naphthyl (Cis and Trans Isomers)

1-(3-naphtylsulfanyl)-2-vinylbenzene (36.7 mg, 0.14 mmol), cuprous chloride (16.7 mg, 0.16 mmol) and (1,3-Bis(2,4,6-trimethylphenyl)-2-imidazolidinylidene)dichloro(phenylmethylene)(tricyclohexylphosphine)ruthenium (119 mg, 0.14 mmol) were dissolved in 6 mL dichloromethane in a 10 mL round-bottom flask under dry nitrogen topped with a reflux condenser. The reaction mixture was refluxed for 5 h. The resulting mixture was evaporated to dryness. The crude product was purified by chromatography on silica gel using 7:3 n-hexane:acetone as eluent to give a green solid (56.0 mg, 55%). Two additional byproducts were separated by chromatography, but only one was fully characterized by NMR analysis: the trans-dichloro isomer as a green solid (8.1 mg, 9%) and an additional green solid (14.2 mg), being probably the six coordinated product with the phosphine ligand still bound. Both byproducts converted with time to the cis isomer according to NMR analysis.

The cis di-chloro isomer: $^1$H-NMR (500 MHz, CD$_2$Cl$_2$): δ 1.75 (s, 3H), 2.18 (s, 3H), 2.26 (s, 3H), 2.49 (s, 3H), 2.61 (s, 3H), 2.74 (s, 3H), 3.88-3.99 (m, 2H), 4.08-4.20 (m, 2H), 6.06 (bs, 1H), 6.73 (dd, J=1.8, 8.7 Hz, 1H), 6.92 (dd, J=1.0, 7.6 Hz, 1H), 6.95 (bs, 1H), 7.03 (m, 2H), 7.14 (d, J=7.7 Hz, 1H), 7.19 (dt, J=0.9, 7.5 Hz, 1H), 7.38 (dt, J=1.2, 7.5 Hz, 1H), 7.49-7.55 (m, 2H), 7.58 (d, J=8.5 Hz, 1H), 7.77-7.80 (m, 2H), 7.83 (d, J=1.8 Hz, 1H), 17.14 (d, J=0.8 Hz, 1H), ppm. $^{13}$C-NMR (125 MHz, CD$_2$Cl$_2$): δ17.90, 18.94, 20.00, 20.46, 21.25, 21.44, 51.93, 52.06, 123.88, 126.77, 127.20, 127.94, 128.07, 128.26, 128.41, 129.72, 129.95, 129.96, 130.05, 130.32, 130.67, 130.97, 132.39, 133.30, 133.56, 134.00, 135.91, 136.07, 137.04, 138.03, 138.99, 139.25, 140.17, 140.46, 155.49, 214.19, 283.94 ppm. ESI m/z (M-Cl)$^+$: Calculated 691.15. found 690.99. Elemental Analysis: Calculated for a monohydrate: C, 61.28; H, 5.41; N, 3.76. Found C, 61.38; H, 5.38; N, 3.47. NMR analysis supports the presence of a water molecule.

The trans di-chloro isomer: $^1$H-NMR (500 MHz, CD$_2$Cl$_2$): δ 2.40 (s, 6H), 2.45 (s, 12H), 4.10 (s, 4H), 6.73 (dd, J=1.8, 8.6 Hz, 1H), 6.88 (dd, J=0.9, 7.7 Hz, 1H), 7.04 (bs, 4H), 7.27 (dt, J=0.9, 7.7 Hz, 1H), 7.32 (d, J=7.7 Hz, 1H), 7.41-7.47 (m, 2H), 7.50-7.53 (m, 2H), 7.65-6.67 (m, 2H), 7.72 (d, J=7.7 Hz, 1H), 17.34 (d, J=0.6 Hz, 1H).

Example 8

Preparation of

1-Bromopyrene

Pyrene (2 g, 9.9 mmol), NBS (1.78 g, 10 mmol) were dissolved in 20 mL of CHCl$_3$ under dry nitrogen topped with a reflux condenser. The reaction was stirred at 65° C. and monitored by GC-MS until complete. After evaporation of the solvent the crude product was further purified by chromatography on silica gel using 20:1 petroleum ether 60-80: EtOAc as eluent to afford a yellow solid (2 gr, 72%). $^1$H-NMR (500 MHz, CD2Cl2): δ 8.02-8.11 (m, 4H), 8.17-8.24 (m, 4H), 8.41 (d, J=9.2 Hz, 1H). $^{13}$C-NMR (125 MHz, CD$_2$Cl$_2$): δ 120.2, 124.4, 125.4, 126.1, 126.2, 126.3, 127.1, 127.6, 128.2, 129.5, 130.0, 130.5, 131.1, 131.2, 131.4, 131.7. EI-MS: m/z M$^+$ Calculated 280.0. found 280.0.

Pyrene-1-thiol

1-Bromopyrene (550 mg, 1.96 mmol) and sodium methanethiolate (480 mg, 6.85 mmol) were dissolved in freshly distilled DMF under dry nitrogen. The reaction was stirred at 150° C. and monitored by GC-MS until complete. After completion 50 mL of HCl 0.1M were added to the reaction mixture and extracted with 3 portions of ether. The organic phase was washed with 2 portions of water. The extracts were dried with magnesium sulfate and evaporated. The crude product was further purified by chromatography on silica gel using 5:1 petroleum ether (60-80):EtOAc as eluent to afford a yellow solid (300 mg, 65%). $^1$H-NMR (500 MHz, toluene-d8, DMSO-d6): δ 7.35 (s, 1H), 8.10-8.37 (m, 8H), 8.67 (d, J=9.2 Hz, 1H). $^{13}$C-NMR (125 MHz, toluene-d8, DMSO-d6): δ 123.7, 123.8, 124.6, 124.9, 125.7, 125.8, 126.3, 127.0, 127.7, 128.6, 130.1, 130.3, 130.6, 130.8, 131.2, 131.7. EI-MS: m/z M$^+$ Calculated 234.0. found 234.0.

2-(pyrene-3-ylthio)-benzaldehyde 2-fluoro-benzaldehyde (477 mg, 3.8 mmol), potassium carbonate (700 mg, 5.0 mmol) and pyrene-1-thiol (300 mg, 1.28 mmol) were dissolved in 15 mL of dry DMF under dry nitrogen, topped with a reflux condenser. The reaction mixture was heated to 130° C. for 24 h. After cooling the mixture was added to 50 mL of saturated potassium carbonate solution, and the mixture was extracted with 3 portions of ether. The extracts were dried with magnesium sulfate and evaporated. The residue of the crude product was further purified by chromatography on silica gel using 10:1 petroleum ether (60-80) and EtOAc as eluent to afford a yellow solid (200 mg, 46%). $^1$H-NMR (500 MHz, CDCl$_3$): δ 6.56 (dd, J=0.8, 7.9 Hz, 1H), 7.07-7.22 (m, 2H), 7.89 (dd, J=1.7, 7.2 Hz, 1H), 8.02-8.28 (m, 8H), 8.58 (d, J=9.2 Hz, 1H), 10.45 (s, 1H). $^{13}$C-NMR (125 MHz, CDCl$_3$): δ 124.7, 124.9, 125.3, 125.5, 125.9, 126.0, 126.4, 127.1, 128.0, 128.7, 129.0, 130.8, 131.0, 132.5, 133.3, 133.4, 133.8, 133.9, 137.0, 143.2, 191.6. EI-MS: m/z M$^+$ Calculated 338.1. found 338.1.

(pyrene-3-yl)-(2-vinylphenyl)sulfane

Methyl triphenylphosphonium iodide (250 mg, 0.62 mmol) was dissolved in 20 mL of dry THF at 0° C. under dry nitrogen. To the mixture was added in one portion potassium tert-butoxide (75 mg, 0.66 mmol) and was stirred for 10 min at room temperature. 2-(pyrene-3-ylthio)-benzaldehyde (150 mg, 0.44 mmol) was added in one portion at 0° C. and the reaction mixture was stirred for additional 5 h at room temperature. The mixture was added to 50 mL of saturated sodium bicarbonate solution, and extracted with 3 portions of ether. The extracts were dried with magnesium sulfate and evaporated. The crude product was further purified by chromatography on silica gel using 20:1 petroleum ether (60-80):EtOAc as eluent to afford a yellow solid (100 mg, 70%). $^1$H-NMR (500 MHz, CDCl$_3$): δ 5.36 (dd, J=1.3, 11.3 Hz, 1H), 5.77 (dd, J=1.3, 17.4 Hz, 1H), 6.92 (dd, J=1.3, 7.8 Hz, 1H), 7.02-7.05 (m, 1H), 7.20-7.23 (m, 1H), 7.37 (dd, J=10.8, 17.4 Hz, 1H), 7.61 (dd, J=1.3, 7.8 Hz, 1H), 7.94 (d, J=8.2 Hz, 1H), 8.01-8.22 (m, 8H), 8.61 (d, J=9.5 Hz, 1H). $^{13}$C-NMR (125 MHz, CDCl$_3$): δ 116.4, 124.4, 124.5, 125.2, 125.3, 125.5, 126.1, 126.2, 126.9, 127.2, 127.8, 128.4, 128.5, 128.9, 130.9, 131.0, 131.1, 131.2, 131.4, 134.3, 137.9. EI-MS: m/z M$^+$ Calculated 336.1. found 336.1.

The Compound of Formula 1A Wherein R is Pyernyl (pyrene-3-yl)-(2-vinylphenyl)sulfane (50 mg, 0.15 mmol), cuprous chloride (16.0 mg, 0.16 mmol) and (1,3-Bis(2,4,6-trimethylphenyl)-2-imidazolidinylidene)dichloro(phenylmethylene)(tricyclohexylphosphine)ruthenium (126 mg, 0.15 mmol) were dissolved in 6 mL dichloromethane in a 10 mL round-bottom flask under dry nitrogen topped with a reflux condenser. The reaction mixture was refluxed for 20 h. The resulting mixture was purified by chromatography on silica gel using 7:3 n-hexane:acetone as eluent to give a green solid (80 mg, 67%). $^1$H-NMR (500 MHz, CD$_2$Cl$_2$): δ 2.11 (s, 3H), 2.12 (s, 3H), 2.15 (s, 3H), 2.43 (s, 3H), 2.49 (s, 3H), 2.52 (s, 3H), 3.92-4.24 (m, 4H), 5.98 (s, 1H), 6.64 (s, 3H), 6.85-6.97 (m, 5H), 7.09-7.12 (m, 1H), 7.19-7.21 (m, 1H), 7.32 (d, J=8.8 Hz, 1H), 7.90 (d, J=8.8 Hz, 1H), 8.02 (d, J=8.8 Hz, 1H), 8.12 (m, 1H), 8.21 (d, J=8.8 Hz, 1H), 8.31-8.36 (m, 1H), 8.81 (d, J=8.8 Hz, 1H), 17.26 (s, 1H). $^{13}$C-NMR (500 MHz, CD$_2$Cl$_2$): δ 17.7, 18.2, 19.6, 19.9, 20.7, 20.8, 51.4, 51.9, 124.4, 125.9, 126.2, 126.4, 127.3, 128.7, 128.9, 129.0, 129.2, 129.3, 129.4, 129.5, 130.2, 130.6, 131.1, 131.9, 133.1, 135.3, 135.6, 136.5, 137.2, 138.6, 139.4, 139.5, 154.5, 213.8, 283.4. ESI m/z (M-Cl)$^+$: Calculated 765.16. found 764.95.

Example 9

Figure 1:
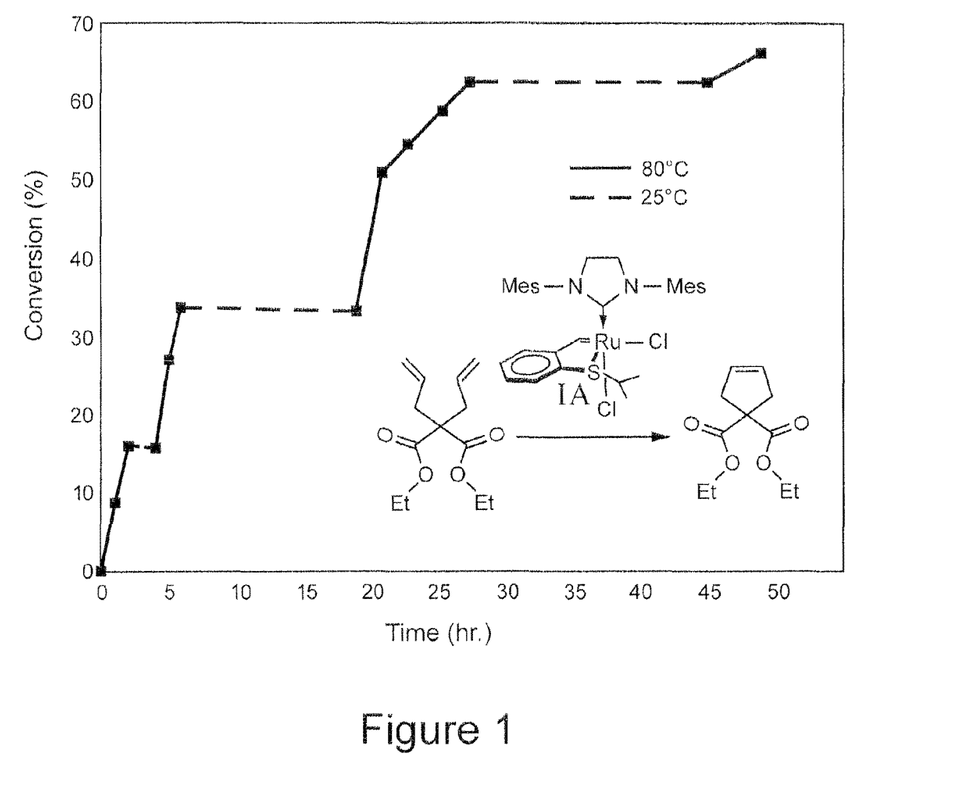
FIG. 1 illustrates the thermo-switchable behavior of the catalyst of Formula IA in RCM reaction. Specifically, conversion of diethyl diallylmalonate by RCM using the catalyst IA at room temperature (dashed line) and at 80 degrees centigrade (solid line) is shown.

The Thermo-Switchable Behavior of the Catalyst of the Invention in Ring Closing Metathesis Reaction Olefin starting material: diene
Catalyst: The compound of Example 1
Reaction: Ring closing metathesis
A 2 ml toluene solution of 0.1M diethyl diallylmalonate and 1 mol % the compound of Example 1 was stirred in a 10 ml round-bottomed flask under dry nitrogen, topped with a reflux condenser. The reaction was carried out with intermittent periods of heating at 80° C. and cooling to 25° C. The progress of the reaction was determined by GC-MS. [GC-MS parameters: initial temperature 80° C., initial time 2 min., maximum temperature 325° C., rate 30 deg/min, equilibration time 0.5 min., final time 8 min., total time 17.33 min. Mode:split 100:1. Inlet temp. 250° C. Detector temp. 300° C. Retention time for diethyl cyclopent-3-ene-1,1-dicarboxylate 5.28 min. Retention time for diethyl diallylmalonate, 5.54 min. The reaction was monitored after 1 hr, 2 hrs, 3 hrs, 4 hrs, 5 hrs, 6 hrs, 7 hrs, 19 hrs, 21 hrs, 23 hrs, 25 hrs, 27 hrs, 45 hrs, 50 hrs, 53 hrs. The reaction was first heated for 2 hours at 80° C., then cooled to room temperature for 2 hours, then heated to 80° C. for two hours, then cooled to room temperature for 15 hours, then heated for 6 hours at 80° C., then cooled for 18 hours, then heated for 8 hours.].

The conversion of the starting material (%) versus the accumulating reaction time (hours) is plotted in FIG. 1. As shown in the figure, at 25° C. the composition of the reaction mixture remains essentially constant whereas at 80° C. appreciable conversion of the starting material was measured, clearly demonstrating the thermo-switchable behavior of the novel catalyst.

Example 10

Figure 2:
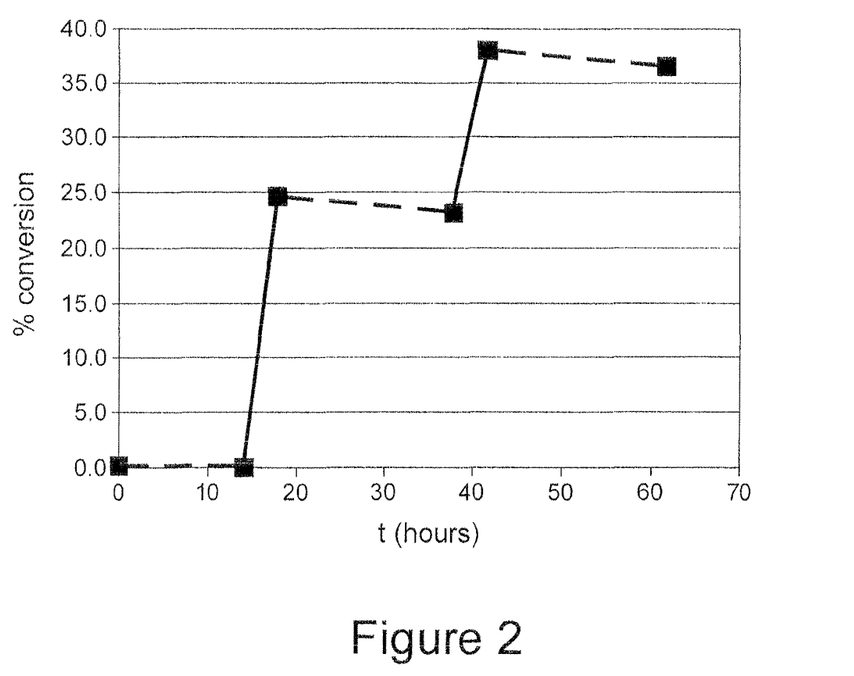
FIG. 2 illustrates the thermo-switchable behavior of the catalyst of Formula IA in ROMP reaction. Specifically, consumption of norbornene derived monomer by ROMP using the catalyst IA at room temperature (dashed line) and at 80 degrees centigrade (solid line) is shown.

The Thermo-Switchable Behavior of the Catalyst of the Invention in Ring-Opening Metathesis Polymerization Olefin starting material: cyclolalkene
Catalyst: The compound of Example 1
Reaction: Ring opening metathesis polymerization
In a 20 ml vial, the monomer dimethyl 5-nonbornene-2,3-dicarboxylate (1.05 g, 5 mmol) was dissolved in 10 ml toluene together with mesitylene as internal standard (1.10 g, 9.15 mmol). In a second 20 ml vial, the catalyst of Example 1 was placed (10 mg, 0.016 mmol). The monomer solution was transferred to the second vial and the reaction mixture was stirred at 25° C. and 80° C. periodically, such that at each period of time, the reaction mixture was held at the selected temperature for approximately 20 minutes. The progress of the reaction was determined by GC-MS. The conversion of the starting material (%) versus the accumulating reaction time (minutes) is plotted in FIG. 2. As shown in the figure, at 25° C. the composition of the reaction mixture remains essentially constant whereas at 80° C. appreciable conversion of the starting material was measured, clearly demonstrating the thermo-switchable behavior of the novel catalyst.

Example 11

The Thermal Activation of the Catalysts of the Invention in Ring Closing Metathesis Reaction Olefin starting material: diene
Catalyst: The compounds of Examples 1-5
Reaction: Ring closing metathesis Thermal activation behavior was tested by stepwise heating a toluene solution of the catalysts in the presence of diethyl diallylmalonate (0.1 M concentration with 1 mol % catalyst). The benchmark ring closing metathesis (RCM) reaction was monitored by GC-MS while quickly raising the temperature by 20° C. every 2 h until a temperature of 100° C. was reached. The results are presented in FIG. 3.

Figure 3:
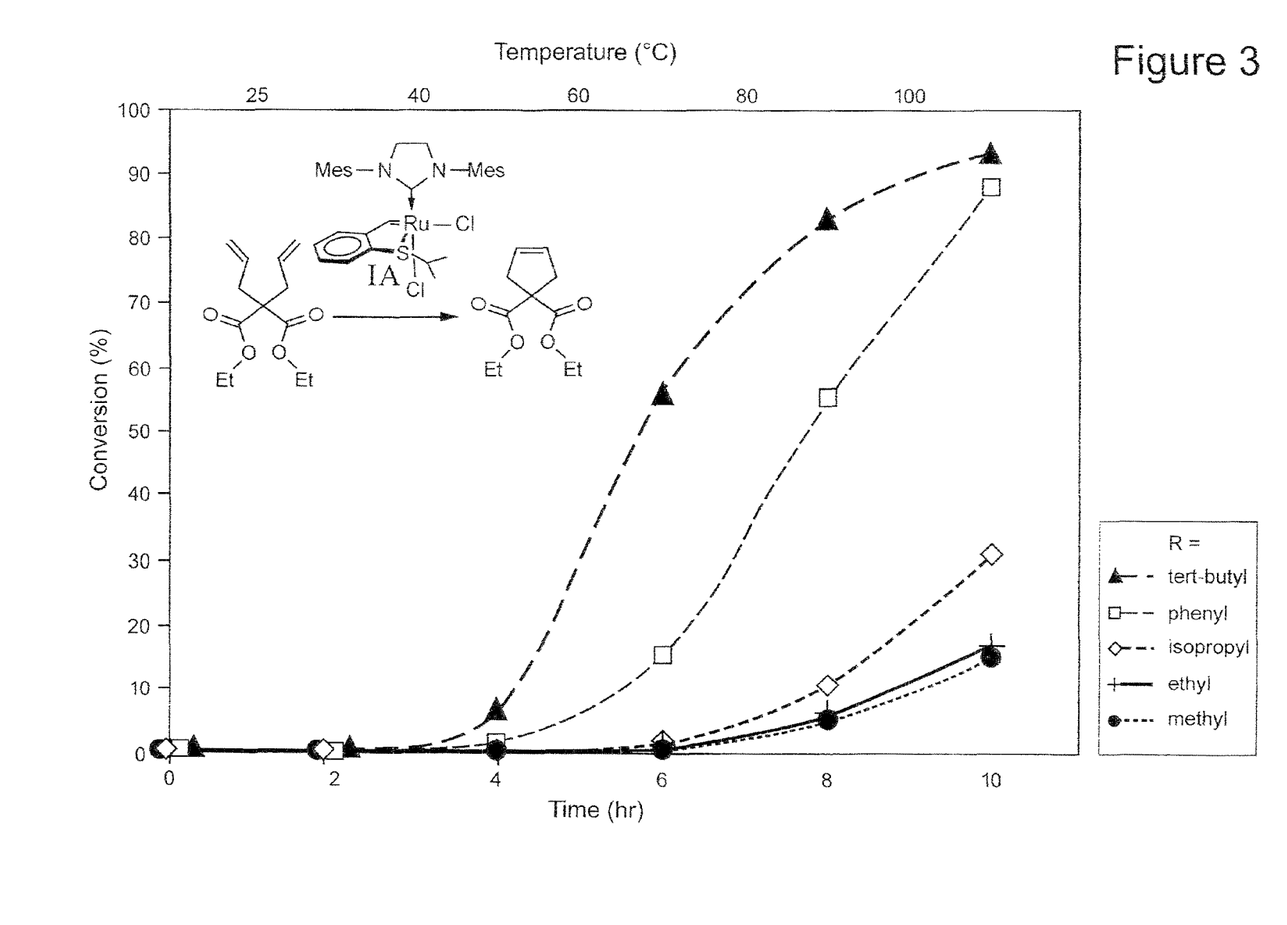
FIG. 3 illustrates the RCM reaction of diethyl diallylmalonate with the catalysts of the invention at increasing temperatures; each 2 h block was kept at constant temperature.

It can be seen from FIG. 3 that the catalysts according to the present invention are essentially inactive at room temperature, and become active by means of heating the reaction mixture to above a threshold temperature. The introduction of bulkier substituents increased the reactivity of the catalyst, such that the threshold temperature for the compounds of Formula IA wherein R is tert-butyl is lower than the corresponding threshold temperature for the compounds wherein R is methyl, ethyl and isopropyl. Among the compounds of the invention, the compound of formula IAc, wherein R is isopropyl, is considered to be especially useful for certain applications, since at room temperature it displays no activity even after two weeks of storage with the olefin, whereas at about 80° C. it accelerates the metathesis reaction effectively.

Example 12

The Light Activation of the Catalysts of the Invention in Ring Closing Metathesis Reaction Olefin starting material: diene
Catalyst: The compounds of Examples 5, 7 and 8
Reaction: Ring closing metathesis An NMR tube was charged with 0.6 ml of $CD_2Cl_2$, the diene starting material (at a concentration of 0.1M) and the catalyst (at a loading of 5% mol). The solution was exposed to UV irradiation (100 W UV lamp at 365 nm) for a period of 5 hours at 28° C. In addition, a similar set of solutions was prepared in order to test the activation induced by visible light (instead of the UV light). Reaction progress was determined by injection to GC-MS after 24 h using mesitylene as an internal standard.

The results for both types of light activation are reported in table 1:

TABLE 1

| Entry | Diene starting material | Catalyst | Product | Yield UV | Yield VIS |
|---|---|---|---|---|---|
| a | $EtO_2C$, $CO_2Et$ diallyl | Example 5 | $EtO_2C$, $CO_2Et$ cyclopentene | 86% | 60% |
| b | $EtO_2C$, $CO_2Et$ diallyl | Example 7 | $EtO_2C$, $CO_2Et$ cyclopentene | 77% | 70% |
| c | $EtO_2C$, $CO_2Et$ diallyl | Example 8 | $EtO_2C$, $CO_2Et$ cyclopentene | 62% | ND |
| d | Ts-N(allyl)(allyl) | Example 5 | N-Ts pyrroline | 85% | 78% |
| e | Ts-N(allyl)(allyl) | Example 7 | N-Ts pyrroline | 78% | 89% |
| f | Ts-N(allyl)(homoallyl) | Example 5 | N-Ts tetrahydropyridine | >99% | 96% |
| g | Ts-N(allyl)(homoallyl) | Example 7 | N-Ts tetrahydropyridine | 97% | 97% |
| h | Ts-N(homoallyl)(homoallyl) | Example 5 | N-Ts azepine | >99% | 95% |
| i | Ts-N(homoallyl)(homoallyl) | Example 7 | N-Ts azepine | 94% | 95% |

(In table 1, Ts indicates a tosyl group). It should be noted that without the light irradiation, the formation of the product was not observed.

Example 13

The Light Activation of the Catalysts of the Invention in Ring Closing Metathesis Reaction: The Correlation Between the Trans-Cis Ratio and the Conversion of the Starting Material The ring closing metathesis reaction of diethyl diallylmalonate (DDM) was carried out in the presence of the catalysts of Examples 5 and 7 as described before. Several solutions were prepared, and each was of the solutions was irradiated by UV light (365 nm) for a different period of time. The cis-dichloro→trans-dichloro isomerization which occurred in each solution was quantified (the ratio between the two isomers was measured by $^1$H-NMR). In addition, the degree of the conversion of the DDM starting material for each solution was measured by GC-MS (the measurements were taken 24 hours after the addition of the DDM starting material to the solution). The results are shown in Table 2.

TABLE 2

| UV irradiation time (hours) | The ratio between the cis and trans isomers | | Conversion of DDM, % | |
|---|---|---|---|---|
| | Example 5 | Example 7 | Example 5 | Example 7 |
| 0 | 100:0 | 100:0 | 0 | 0 |
| 0.5 | 47:1 | 157:1 | 21 | 6 |
| 1 | 10:1 | 60:1 | 39 | 13 |
| 5 | 3:1 | 5.5:1 | 85 | 74 |
| 10 | 2.6:1 | 6:1 | 86 | 65 |

The results reported in Table 2 illustrate that the higher the amount of the trans isomer in the reaction mixture, the greater is the degree of conversion of the starting material. The correlation found between the amount of the trans isomer generated in the reaction mixture following the UV irradiation, and the conversion of the starting material, allows the practitioner to suitably adjust the time period of the irradiation in order to maximize the amount of the trans isomer, and hence the degree of conversion of the starting material.

Example 14

The Light Activation of the Catalysts of the Invention in Ring-Opening Metathesis Polymerization Olefin starting material: cyclolalkene monomer
Catalyst: The compounds of Example 5 and 7
Reaction: Ring opening metathesis polymerization A 10 mm NMR tube with a magnetic stirrer was charged with 2 mL of $CH_2Cl_2$, the monomer (1 mmol), the catalyst (3.33 μmol, 0.3% loading), and mesitylene as an internal standard (200 mg). The solution was irradiated by UV light (100 W UV lamp at 365 nm) at 28° C. for 5 h period. The resulting mixture was stirred for 24 h. Reaction progress was determined by injection to GC-MS after 24 h. The polymer product is isolated by pouring a sample from the reaction mixture in ether, filtering, and washing the white gum with ether (all color is removed by washing), followed by 12 hour-drying under high vacuum. The resulting polymer was characterized by GPC and NMR analyses.

The monomers which were polymerized, and the degree of conversion are represented in table 3 (conversions were calculated by the reduction in monomer concentration as determined by CG-MS):

TABLE 3

| Entry | Monomer | Catalyst | Conversion of the monomer |
|---|---|---|---|
| a | 5-nonbornene-2,3-dicarboxylate | Example 5 | 40% |
| b | 5-nonbornene-2,3-dicarboxylate | Example 7 | 66% |
| c | Cyclooctene | Example 5 | 96% |
| d | Cyclooctene | Example 7 | >99% |
| e | 1,5-cyclooctadiene | Example 5 | 86% |
| f | 1,5-cyclooctadiene | Example 7 | 84% |

Example 15

Controlling the Progress of a Ring Closing Metathesis Reaction

Figure 4:
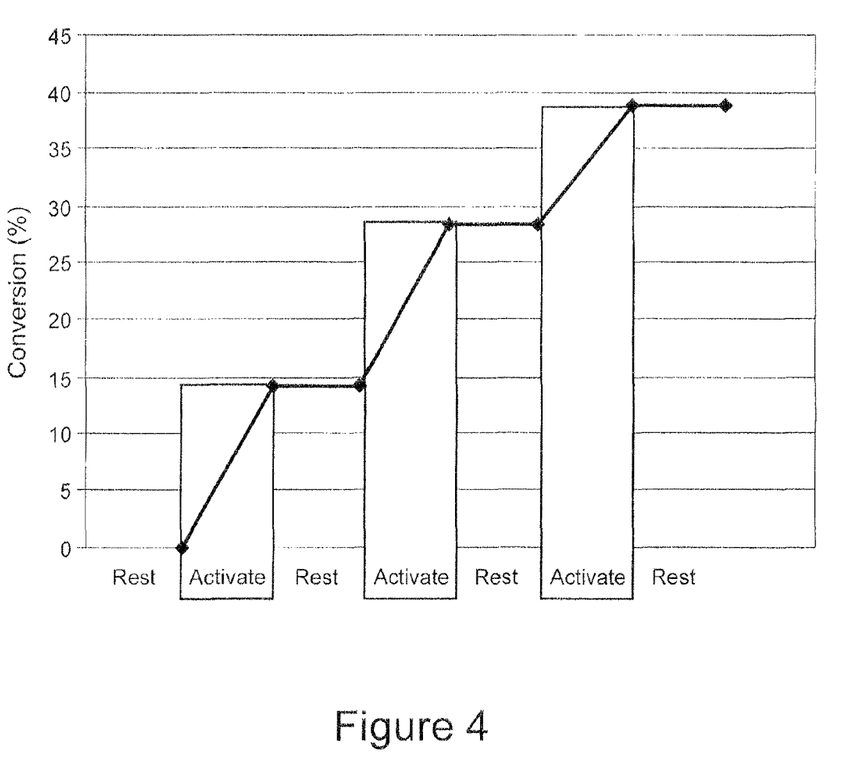
FIG. 4 illustrates a profile of RCM reaction of diethyl diallylmalonate in the presence of a catalyst of Formula I under specific activation-deactivation protocol.

An NMR tube was charged with 0.6 ml of $C_2D_2Cl_4$, the starting material diethyl diallylmalonate (at a concentration of 0.1M) and the catalyst of Example 7 (at a loading of 5 mol %). The solution was irradiated at 28° C. for 15 minutes (100 W UV lamp at 365 nm), followed by 5 minutes heating to 80° C. The conversion of the starting material, which was measured after 24 hours at room temperature, was about 15%. It has been found that the 5 minutes heating period allows an essentially complete transformation of the trans isomer present in the reaction mixture into the cis isomer, and hence the termination of the reaction. Thus, when the reaction mixture is periodically subjected to light irradiation (15 minutes) and subsequent heating (5 minutes at 800), with an intermission of four hours at room temperature between each irradiation-heating cycle, then the reaction has the profile illustrated in FIG. 4 (where the "activate" corresponds to the irradiation-heating cycle, and the "rest" to the intermission period).

The invention claimed is:

1. A sulfur chelated ruthenium compound represented by the following formula:

(I)

wherein M indicates the ruthenium metal bound to a benzylidene carbon; R represents an optionally substituted aryl; $X_1$ and $X_2$ each independently represent halogen; $Y_1$ and $Y_2$ each independently denote unsubstituted or alkyl-substituted phenyl; and independently represents hydrogen, electron withdrawing or electron donating substituent, with m being an integer from 1 to 4.

2. A compound according to claim 1 represented by Formula IA:

(IA)

wherein R is an optionally substituted aryl.

3. A compound according to claim 2, wherein R is an optionally substituted aryl selected from the group consisting of phenyl, naphthyl and pyrenyl.

4. A compound according to claim 1, wherein one Z substituent is nitro and the others are hydrogen.

5. A composition comprising an olefin starting material dissolved in an organic solvent together with a catalytically effective amount of the compound of Formula I as defined in claim 1, wherein said composition is chemically stable at room temperature, such that the conversion of the olefin starting material through metathesis reaction into a product is substantially prevented at room temperature.

6. A composition according to claim 5, wherein the compound of Formula I is a compound of formula IA as defined in claim 2.

7. A process for preparing a metathesis reaction product, which comprises subjecting an olefin to a metathesis reaction in the presence of a catalytically effective amount of a sulfur chelated ruthenium compound represented by the following formula:

(I)

wherein M indicates the ruthenium metal bound to a benzylidene carbon; R represents an optionally substituted aryl; $X_1$ and $X_2$ each independently represent halogen; $Y_1$ and $Y_2$ each independently denote unsubstituted or alkyl-substituted phenyl; and Z independently represents hydrogen, electron withdrawing or electron donating substituent, with m being an integer from 1 to 4;

and irradiating said catalyst of Formula I with light.

8. A process according to claim 7, which comprises adjusting the irradiation period in order to maximize the amount of the trans isomer of the compound of formula (I) in the reaction mixture.

9. A process according to claim 7, which further comprises terminating the reaction by means of heating the reaction mixture.

10. A compound according to claim 3 represented by the following formula:

11. A compound according to claim 3 represented by the following formula:

12. A compound according to claim 3 represented by the following formula:

13. A process according to claim 7, wherein the catalyst used is represented by Formula IA:

(IA)

wherein R is an optionally substituted aryl.

14. A process according to claim 13, wherein the catalyst used is selected from the group consisting of:

* * * * *